United States Patent [19]

Sitzmann

[11] Patent Number: 5,214,189
[45] Date of Patent: May 25, 1993

[54] N-(2-HYDROXYETHYL NITRATE)-2,4,6,-TRINITROBENZAMIDE

[75] Inventor: Michael E. Sitzmann, Adelphi, Md.

[73] Assignee: The United States of America as represented by the Secretary of the Navy, Washington, D.C.

[21] Appl. No.: 901,623

[22] Filed: Jun. 15, 1992

[51] Int. Cl.$^5$ .................. C07C 233/12; C07C 233/16
[52] U.S. Cl. .................................. 558/482; 558/480; 564/166
[58] Field of Search ................. 558/482, 480; 564/166

[56] References Cited

U.S. PATENT DOCUMENTS

| | | | |
|---|---|---|---|
| 3,419,620 | 12/1968 | Becker et al. | 558/482 |
| 3,544,630 | 12/1970 | Frankel et al. | 564/166 |
| 3,928,374 | 12/1975 | Heeres et al. | 548/328.5 |
| 4,703,055 | 10/1987 | Franceschini et al. | 514/400 |
| 5,081,255 | 1/1992 | Sitzmann | 548/145 |

Primary Examiner—Robert L. Stoll
Assistant Examiner—C. Sayala
Attorney, Agent, or Firm—Kenneth E. Walden; Roger D. Johnson

[57] ABSTRACT

N-(2-Hydroxyethyl nitrate)-2,4,6-trinitrobenzamide which is an explosive with good thermal stability at 150° C.

2 Claims, No Drawings

N-(2-HYDROXYETHYL NITRATE)-2,4,6,-TRINITROBENZAMIDE

BACKGROUND OF THE INVENTION

This invention relates to energetic aromatic compounds and more particularly to energetic aromatic nitrate esters.

Missile systems often require explosives that can withstand short-term (30 minutes) exposure to temperatures in the vicinity of 150° C. and above due to aerodynamic heating. Pentaerythritol tetranitrate (PETN) is the highest melting of the commonly available nitrate esters, but its melting point (140° C.) precludes its use in such missiles. U.S. Pat. No. 5,081,255 titled, "High Melting Aromatic Nitrate Esters," which issued to Michael E. Sitzmann on Jan. 14, 1992, discloses several higher melting nitrate esters. These esters generally contain one or more —NHCH$_2$CH$_2$ONO$_2$ amine groups attached to the aromatic ring. The —NHCH$_2$CH$_2$ONO$_2$ groups in the aromatic nitrate esters are produced by nitration of —NHCH$_2$CH$_2$OH substituents on the aromatic ring. It can sometimes be difficult to control the nitration of —NHCH$_2$CH$_2$OH so that the initially formed NHCH$_2$CH$_2$ONO$_2$ groups are not further nitrated (N-nitration) to give —N(NO$_2$)CH$_2$CH$_2$ONO$_2$. The —N(NO$_2$)CH$_2$CH$_2$ONO$_2$ group is often not desirable because it tends to produce lower melting and less stable aromatic nitrate esters compared to —NHCH$_2$CH$_2$ONO$_2$.

It would be desirable to provide energetic aromatic esters that are easier to produce and which have greater thermal stability than those presently available.

SUMMARY OF THE INVENTION

Accordingly, an object of this invention is to provide a new energetic aromatic nitrate ester.

Another object of this invention is to provide a new energetic aromatic nitrate ester having greater thermal stability.

A further object of this invention is to provide a new thermally stable, energetic aromatic nitrate ester that is easier to produce and isolate in greater yield.

These and other objects of this invention are accomplished by providing:

N-(2-hydroxyethyl nitrate)-2,4,6-trinitrobenzamide.

In the method of preparation, one mole of ethanolamine is reacted with each mole of 2,4,6-trinitrobenzoyl chloride to produce N-(2-hydroxyethyl)-2,4,6-trinitrobenzamide which is then nitrated to form the desired N-(2-hydroxyethyl nitrate)-2,4,6-trinitrobenzamide.

DETAILED DESCRIPTION OF THE PREFERRED EMBODIMENT

N-(2-Hydroxyethyl nitrate)-2,4,6-trinitrobenzamide (I),

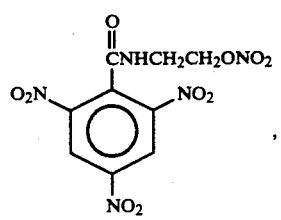

is prepared by nitrating N-(2-hydroxyethyl)-2,4,6-trinitrobenzamide (II),

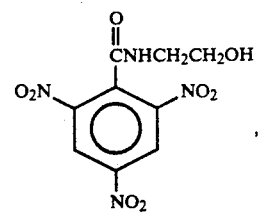

as illustrated by examples 2 and 3. By using 90% nitric acid at a temperature of 0° C. or below, the nitrate ester is formed while N-nitration (formation of a nitramine) is avoided. This is important because formation of N-nitro—N-(2-hydroxyethyl nitrate)-2,4,6-trinitrobenzamide will contaminate and lower the yield of the desired product N-(2-hydroxyethyl nitrate)-2,4,6-trinitrobenzamide. These two compounds would also be very difficult to separate.

Example 1 demonstrates a method of preparing the N-(2-hydroxyethyl)-2,4,6-trinitrobenzamide used as a starting material in the preparation of N-(2-hydroxyethyl nitriate-2,4,6-trinitrobenzamide in examples 2 and 3.

A comparison of examples 2 and 3 with example 5 demonstrates the advantages of amide compounds with the —C(=O)NHCH$_2$CH$_2$ONO$_2$ group over the corresponding amine compounds with the —NHCH$_2$CH$_2$ONO$_2$ group. In examples 2 and 3, N-(2-hydroxyethyl)-2,4,6-trinitrobenzamide was nitrated to form N-(2-hydroxyethyl nitrate)-2,4,6-trinitrobenzamide in yields of 87 and 94 percent. Even nitration at a temperature as high as 0° C. (example 3) produced an excellent yield, (94 percent) with low impurities. In contrast, in example 5, the corresponding amine, N-(2-hydroxyethyl)-2,4,6-trinitroaniline when nitrated at −25° C. produced N-(2-hydroxyethyl nitrate)-2,4,6-trinitroaniline in only an 11 percent yield. Moreover a substantial amount of the undesirable, less stable N-nitro—N-(2-hydroxyethyl nitrate)-2,4,6-trinitroaniline, was produced, making purification difficult. It would appear that control of nitration for —C(=O)NHCH$_2$CH$_2$OH is considerably easier than for —NHCH$_2$CH$_2$OH because the electronegative carbonyl (C=O) readily.

A second advantage of the amide N-(2-hydroxyethyl nitrate)-2,4,6-trinitrobenzamide over the corresponding amine N-(2-hydroxyethyl nitrate)-2,4,6-trinitroaniline is seen in the melting points. As demonstrated by examples 2 and 3, the melting point of the amide is about 200° C. In contrast, example 5 shows the melting point of the corresponding amine to be less than 100° C. Thus the amide is suitable for high temperature use in a missile warhead whereas the amine is not. The melting point (203° C.) of a sample of N-(2-hydroxyethyl nitrate)-2,4,6-trinitrobenzamide did not change after it was held at 150° C. for one hour.

The general nature of the invention having been set forth, the following examples are presented as specific illustrations thereof It will be understood that this invention is not limited to these specific examples, but is susceptible to various modifications that will be recognized by one of ordinary skill in the art.

EXAMPLE 1

N-(2-Hydroxyethyl)-2,4,6-trinitrobenzamide (II)

Ethanolamine (0.95g, 0.016 mole) in 16 ml of methanol was stirred well in a dry ice-acetone bath ($-78°$ C.) during the rapid g dropwise addition of a solution containing 2.1 g (0.008 mole) of 2,4,6-trinitrobenzoyl chloride in 7 ml of 1,4-dioxane. The thick mixture was allowed to warm to room temperature before the volatiles were removed (under reduced pressure) to give a dark semisolid residue that was stirred with 15 ml of cold water The insoluble solid was removed, washed with a small amount of cold water, and then stirred with methylene chloride (15 ml) to give 1.40g (61%) of insoluble solid product, N-(2-hydroxyethyl)-2,4,6-trinitrobenzamide, mp 189°–191° C. $^1$H NMR (acetone-$d_6$): 3.62 (t, 2H), 3.80 (t, 2H), 9.36 (s, 2H). IR (KBr): 3500–3250 (NH, OH), 1655 (C=O), 1550 ($NO_2$).

EXAMPLE 2

N-(2-Hydroxyethyl nitrate)-2,4,6-trinitrobenzamide (I) by nitration at $-25°$ C.

To 8 ml of 90% nitric acid stirred at $-40°$ C. was added 1.39 g (0.0043 mole) of N-(2-hydroxyethyl)-2,4,6-trinitrobenzamide rapidly in portions. The reaction mixture was allowed to warm to $-30°$ to $-25°$ C. and held for 5 minutes at which time all material was in solution The solution was poured onto ice to give 1.3g (87%) of tan solid product, N-(2-hydroxyethyl nitrate)-2,4,6-trinitrobenzamide, mp 197° C. dec. Crystallization from acetone-methanol gave 1.1 g, mp 203° C. dec; $^1$H NMR (acetone-$d_6$): 3.93 (m, 2H), 4.90 (t, 2H), 9.40 (s, 2H). IR (KBr): 3130 (NH), 1665 (C=O), 1630–1610 ($ONO_2$), 1580, 1555 ($NO_2$). Anal. Calcd for $C_9H_7N_5O_{10}$: C, 31.31; H, 2.04; N, 20.29. Found C, 31.73; H, 2.05; N, 20.36.

EXAMPLE 3

N-(2-Hydroxyethyl nitrate)-2,4,6-trinitrobenzamide (I) by nitration at 0° C.

To 90% nitric acid (1.5 ml) stirred at $-5°$ C. was added 0.15 g of N-(2-hydroxyethyl)-2,4,6-trinitrobenzamide. After 5 minutes at $-5°$ to 0° C. the solution was poured on ice to give 0.16 g (94%) of product, N-(2-hydroxyethyl nitrate)-2,4,6-trinitrobenzamide, mp 196° C. dec.

EXAMPLE 4

N-(2-Hydroxyethyl)-2,4,6-trinitroaniline

Ethanolamine (0.6g, 0.01 mole) in 10 ml of methanol was stirred in an ice bath as 2.4g (0.01 mole) of 2,4,6-trinitroanisole was added rapidly in portions. After 15 minutes at 0° C., the solution was allowed to stand for 3 hours at room temperature before it was cooled in ice to give 1.85g (69%) of crystals of product, N-(2-hydroxyethyl)-2,4,6-trinitroaniline, mp 108°–110° C.: $^1$H NMR (acetone - $d_6$+$D_2O$): 3.33 (t, 2H), 3.96 (t, 2H), 9.03 (s, 2H).

EXAMPLE 5

N-(2-Hydroxyethyl nitrate)-2,4,6-trinitroaniline

To 90% nitric acid (8 ml) stirred at $-40°$ C. was added 0.8g (0.003 mole) of N-(2-hydroxyethyl)-2,4,6-trinitroaniline. The solution was allowed to warm to $-35°$ to $-30°$ C. for 5 minutes before it was poured onto ice to give 1.0g of product. Thin-layer chromatography indicated the product contained the desired material, N-(2-hydroxyethyl nitrate)-2,4,6-trinitroaniline, along with some starting material and a substantial amount of N-nitro—N-(2-hydroxyethyl nitrate)-2,4,6-trinitroaniline. The product was stirred with methylene chloride (10 ml) at room temperature and the insoluble solid (0.6g of N-nitro—N-(2-hydroxyethyl nitrate)-2,4,6-trinitroaniline, mp 122° C.) was removed by filtration. The filtrate was cooled to $-20°$ C. to give 0.1 g (11%) of crystals of the product N-(2-hydroxyethyl nitrate)-2,4,6-trinitroaniline, mp 90°–94° C. Recrystallization from methylene chloride raised the melting point to 94°–96° C.; $^1$H NMR (acetone-$d_6$+$D_2O$): 3.73 (t, 2H), 5.05 (t, 2H), 9.25 (s, 2H).

Anal. Calcd for $C_8H_7N_5O_9$: C, 30.29; H, 2.22; N, 22.08. Found C, 30.60; H, 2.36; N, 21.77.

Obviously numerous modifications and variations of the present invention are possible in light of the above teachings. It is therefore to be understood that within the scope of the appended claims the invention may be practiced otherwise than as specifically described herein.

What is claimed as new and desired to be secured by Letters Patent of the U.S. is:

1. N-(2-hydroxyethyl nitriate)-2,4,6-trinitrobenzamide.
2. N-(2-hydroxyethyl)-2,4,6-trinitrobenzamide.

* * * * *